(12) United States Patent  
Ghosh et al.

(10) Patent No.: US 8,969,643 B2
(45) Date of Patent: Mar. 3, 2015

(54) METHOD FOR CONVERSION OF AROMATIC HYDROCARBONS

(71) Applicants: Ashim Kumar Ghosh, Houston, TX (US); Pamela Harvey, Missouri, TX (US); Neeta Kulkarni, Houston, TX (US); Manuel Castelan, Pear Land, TX (US)

(72) Inventors: Ashim Kumar Ghosh, Houston, TX (US); Pamela Harvey, Missouri, TX (US); Neeta Kulkarni, Houston, TX (US); Manuel Castelan, Pear Land, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 121 days.

(21) Appl. No.: 13/900,633

(22) Filed: May 23, 2013

(65) Prior Publication Data

US 2014/0350315 A1    Nov. 27, 2014

(51) Int. Cl.
*C07C 4/18*   (2006.01)
*C07C 5/22*   (2006.01)

(52) U.S. Cl.
CPC .................................... *C07C 4/18* (2013.01)
USPC ........... 585/486; 585/488; 585/489; 585/319; 585/481

(58) Field of Classification Search
USPC ........................ 585/486, 488, 489, 319, 481
See application file for complete search history.

(56) References Cited

U.S. PATENT DOCUMENTS

| | | |
|---|---|---|
| 7,060,864 B2 | 6/2006 | Ghosh et al. |
| 7,084,318 B2 | 8/2006 | Ghosh et al. |
| 7,105,713 B2 | 9/2006 | Ghosh et al. |
| 7,196,237 B2 | 3/2007 | Ghosh et al. |
| 7,244,869 B2 | 7/2007 | Ghosh et al. |
| 7,279,608 B2 | 10/2007 | Ghosh et al. |
| 7,285,511 B2 | 10/2007 | Ghosh et al. |
| 7,304,194 B2 | 12/2007 | Ghosh et al. |
| 7,368,410 B2 | 5/2008 | Ghosh et al. |
| 7,399,727 B2 | 7/2008 | Ghosh et al. |
| 7,446,069 B2 | 11/2008 | Ghosh et al. |
| 7,507,685 B2 | 3/2009 | Ghosh et al. |
| 7,560,608 B2 | 7/2009 | Ghosh et al. |
| 7,576,026 B2 | 8/2009 | Ghosh et al. |
| 7,629,498 B2 | 12/2009 | Brown et al. |
| 7,635,793 B2 | 12/2009 | Ghosh et al. |
| 7,662,737 B2 | 2/2010 | Ghosh et al. |
| 7,674,942 B2 | 3/2010 | Ghosh et al. |
| 7,713,898 B2 | 5/2010 | Ghosh et al. |
| 8,062,987 B2 | 11/2011 | Ghosh et al. |
| 8,115,041 B2 | 2/2012 | Ghosh et al. |
| 2009/0000988 A1 | 1/2009 | Brown et al. |

(Continued)

FOREIGN PATENT DOCUMENTS

| | | |
|---|---|---|
| CN | 102463085 A | 5/2012 |
| CN | 102464540 A | 5/2012 |

(Continued)

*Primary Examiner* — Thuan D Dang
(74) *Attorney, Agent, or Firm* — Gino C. Catena; Grady K. Bergen; Griggs Bergen LLP

(57) ABSTRACT

A method of converting hydrocarbons requires contacting a hydrocarbon stream containing alkylated aromatic hydrocarbons with a catalyst of a phosphorus-containing pentasil zeolite in a reactor. The phosphorus-containing pentasil zeolite having a phosphorus content of 7.5% or less by weight of zeolite, a pore volume of at least 0.2 ml/g, and a $^{27}$Al MAS NMR spectrum characterized by a peak at or near 50 ppm that is greater than any other peak in said spectrum. A benzene-enriched output stream is recovered from the reactor.

20 Claims, 2 Drawing Sheets

(56) References Cited

U.S. PATENT DOCUMENTS

2009/0253949 A1 10/2009 Ghosh et al.
2010/0305378 A1 12/2010 Galloway, Jr. et al.
2011/0137099 A1 6/2011 Ghosh et al.

FOREIGN PATENT DOCUMENTS

| CN | 102464558 A | 5/2012 |
| CN | 102464559 A | 5/2012 |
| CN | 102464561 A | 5/2012 |
| WO | WO2004000768 A1 | 12/2003 |
| WO | WO2004000974 A1 | 12/2003 |

US 8,969,643 B2

METHOD FOR CONVERSION OF AROMATIC HYDROCARBONS

TECHNICAL FIELD

The invention relates generally to the conversion of hydrocarbons, and in particular to the conversion of aromatic hydrocarbons into particular products.

BACKGROUND

Ethylene production through thermal cracking methods, such as steam cracking of naphtha, produces several byproducts. Among these byproducts are those $C_{5+}$ hydrocarbons, which are often referred to as pyrolysis gasoline or "pygas." Such pygas typically contains aromatics and paraffins. Pygas is often sold and traded as a commodity that may be further treated or processed. Benzene is a major component of such pygas and is often separated from other aromatics, such as toluene, mixed xylene, ethylbenzene and $C_{9+}$ aromatics, which results in a benzene-depleted product. This benzene-depleted aromatic product may be sold without further processing. The benzene-depleted aromatic product containing toluene, mixed xylene, ethylbenzene, $C_{9+}$ aromatics, and other impurities, can be further processed or upgraded, however, to produce more valuable products.

The present invention is therefore directed to a catalyst and method of converting hydrocarbon products, such as benzene-depleted aromatic products, to produce higher value products.

SUMMARY

A method of converting hydrocarbons is carried out by contacting a hydrocarbon stream containing alkylated aromatic hydrocarbons with a catalyst of a phosphorus-containing pentasil zeolite in a reactor. The phosphorus-containing pentasil zeolite is that having (i) a phosphorus content of 7.5% or less by weight of zeolite; (ii) a pore volume of at least 0.2 ml/g; and (iii) a $^{27}Al$ MAS NMR spectrum characterized by a peak at or near 50 ppm that is greater than any other peak in said spectrum. A benzene-enriched output stream is recovered from the reactor.

In particular embodiments, the hydrocarbon stream contains benzene in an amount of less than 15% by weight of the feed and at least one of toluene, $C_8$ aromatics, and $C_{9+}$ aromatics in an amount totaling 50% or more by weight of the hydrocarbon stream. In some embodiments, benzene is separated from the benzene-enriched output stream to form a benzene product stream and a second output stream. In certain applications, the second output stream may be contacted with a xylene-selective catalyst in a second reactor to form a xylene-enriched output stream. Xylene may be further separated from the xylene-enriched output stream to form a xylene product stream.

In those embodiments where a xylene selective catalyst is used, the xylene catalyst may be a second phosphorus-containing zeolite that is bound with an inorganic binder, the second phosphorus-containing zeolite of the xylene selective catalyst having at least two $^{31}P$ MAS NMR peaks with maxima at from 0 ppm to −55 ppm, with at least one $^{31}P$ MAS NMR peak having a maximum at from −40 ppm to −50 ppm.

In some instances, the first phosphorus-containing pentasil zeolite has a phosphorus content of 0.1 to 4.5% by weight of zeolite. In others, the first phosphorus-containing pentasil zeolite has a phosphorus content of 0.1 to 2% by weight of zeolite. In some embodiments, the first phosphorus-containing pentasil zeolite has a silica to alumina molar ratio of at least 25. And in others, the first phosphorus-containing pentasil zeolite has a silica to alumina molar ratio of at least 200.

In certain applications, the hydrocarbon stream is a benzene-depleted pyrolysis gasoline stream.

The hydrocarbon stream may contain toluene in an amount of from 40% to 65% by weight of the hydrocarbon stream in some embodiments. In certain embodiments, the hydrocarbon stream may contain $C_8$ aromatics in an amount of from 20% to 30% by weight of the hydrocarbon stream. The hydrocarbon stream may contain $C_{9+}$ aromatics in an amount of from 5% to 20% by weight of the hydrocarbon stream.

In specific embodiments, the hydrocarbon stream is a pyrolysis gasoline stream. The pyrolysis gasoline stream may contain benzene in an amount of less than 15% by weight of the feed and at least one of toluene, $C_8$ aromatics, and $C_{9+}$ aromatics in an amount totaling 50% or more by weight of the hydrocarbon stream. Benzene may be separated from the benzene-enriched output stream to form a benzene product stream and a second output stream, in some instances. The second output stream may be further contacted with a xylene-selective catalyst in a second reactor to form a xylene-enriched output stream, in some applications. Xylene may be separated from the said xylene-enriched output stream to form a xylene product stream, in such cases.

In those applications where the hydrocarbon stream is a pyrolysis gasoline stream, the xylene selective catalyst may be a second phosphorus-containing zeolite bound with an inorganic binder, the second phosphorus-containing zeolite of the xylene selective catalyst having at least two $^{31}P$ MAS NMR peaks with maxima at from 0 ppm to −55 ppm, with at least one $^{31}P$ MAS NMR peak having a maximum at from −40 ppm to −50 ppm.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
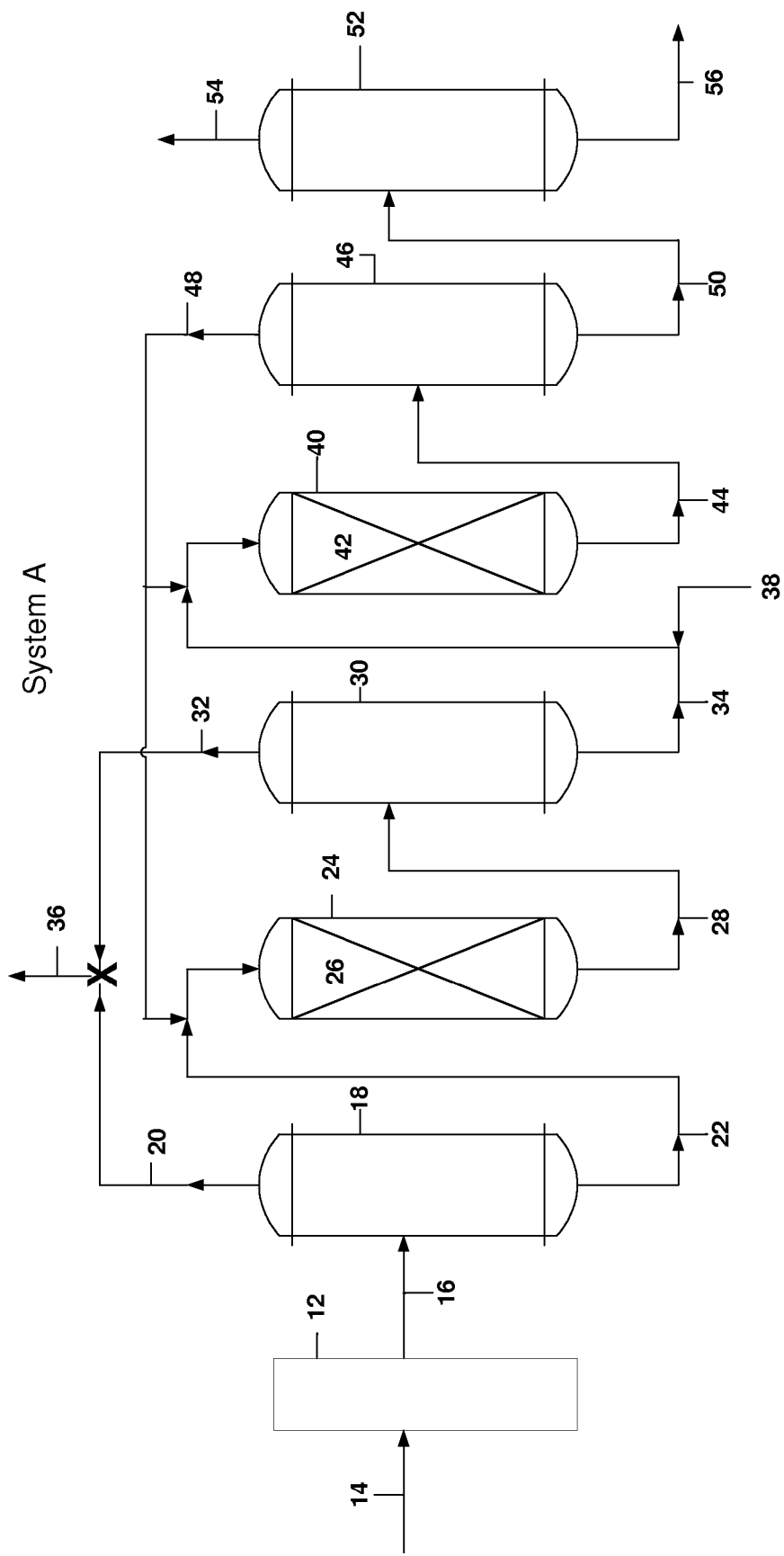
FIG. 1 is a flow schematic of a system for the conversion of hydrocarbons in accordance with an embodiment of the invention.

As used herein, "a" or "an" means one or more, with the singular encompassing the plural or the plural encompassing the singular unless expressly stated otherwise or is otherwise clear from the context. For example, the statement "contacting with a catalyst" should be understood to mean "contacting with one or more catalysts."

The present invention is directed to the conversion of feed or feedstock containing aromatic hydrocarbons. Such aromatic hydrocarbon feedstock may include benzene, toluene, $C_8$ aromatics (e.g., mixed xylene and ethylbenzene), and $C_{9+}$ aromatics. The aromatic-containing hydrocarbon feedstock may also include other non-aromatic hydrocarbons, such as straight-chain, branched chain, and cyclic compounds, which may be saturated or unsaturated.

The aromatic-containing feedstock may be those provided from petroleum gasoline or "pygas." Pygas is a byproduct of olefin production by thermal cracking, such as steam cracking of hydrocarbon, particularly in the cracking of naphtha of petroleum feedstock. Various pygas feedstocks, their derivation and examples of their compositions are described in U.S. Pat. No. 7,629,498, which is herein incorporated by reference in its entirety for all purposes. Such feedstocks described in U.S. Pat. No. 7,629,498 may also be used in the hydrocarbon conversion process described herein. Pygas compositions may vary and may depend upon the severity of the cracking operation and the compositions of the feedstocks used in the cracking. As an example, however, a typical pygas composition may have a benzene content of from 15% to 65%, a toluene content of from 5% to 35%, a $C_8$ aromatic content of 1% to 15%, a $C_{9+}$ aromatic content of less than about 1%, and a non-aromatic hydrocarbon content of from about 1% to 22%, all based on total weight of the pygas. Other aromatic-containing feedstocks that are non-pygas feedstocks having similar compositions may also be used in the conversion methods described herein. Accordingly, the present invention may extend to the conversion and treatment of both pygas and non-pygas feedstocks, which may have similar compositions.

It should be understood that with respect to any concentration or amount range listed or described in the Summary and Detailed Description as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

The present invention, although applicable more broadly, may have particular application to the conversion of benzene-depleted hydrocarbon feedstocks. As used herein, the expression "benzene-depleted" refers to those products, hydrocarbon feedstocks or feeds containing benzene in an amount of less than 15% by weight of the product or feedstock and containing 50% or more by weight of product or feedstock of alkylated aromatic compounds. Such alkylated aromatic compounds may include toluene, $C_8$ aromatics (e.g., mixed xylene and ethyl benzene), and $C_{9+}$ aromatics. The benzene-depleted feedstock may also include other non-aromatic hydrocarbons, such as straight-chain, branched chain, and cyclic compounds, which may be saturated or unsaturated.

Such benzene-depleted hydrocarbon feedstocks may include those pygas feedstocks, or other products or feedstocks that have been further processed to remove benzene. Benzene may be separated or extracted from such products or feedstocks, such as through distillation or other suitable separation techniques, to provide a benzene-rich product and a benzene-depleted product. This benzene-depleted products may be used as a feed or feedstock that may be further converted or processed using the methods described herein.

In certain embodiments, the benzene-depleted feedstock may be that containing benzene in an amount of from 0.5% to less than 15% by weight of the feedstock. In other embodiments, the benzene-depleted feedstock may be that containing benzene in an amount of from 14%, 13%, 12%, 11%, 10%, 9%, 8%, 7%, 6%, 5%, 4%, 3%, 2%, 1% or less by weight of the feedstock. In particular embodiments, the benzene-depleted product or feedstock is that having a benzene content of from 5%, 4%, 3%, 2%, 1% or less by weight.

With respect to the alkylated aromatic compounds making up the benzene-depleted feedstock or feed, such alkylated aromatic compounds may include toluene in an amount of from 65% or less by weight of the feedstock. In certain embodiments, the toluene may be present in any amount range within the amounts of 5%, 10%, 15%, 20%, 25%, 30%, 35%, 40%, 45%, 50%, 55%, or 65% by weight of the feedstock.

The benzene-depleted feedstock or feed may contain $C_8$ aromatic compounds, such as xylene and ethylbenzene, in an amount of from 40% or less by weight of the feedstock. In certain embodiments, the $C_8$ aromatic compounds may be present in any amount range within the amounts of 1%, 2%, 3%, 4%, 5%, 6%, 7%, 8%, 9%, 10%, 15%, 20%, 25%, 30, or 40% by weight of the feedstock.

The benzene-depleted feedstock or feed may contain $C_{9+}$ aromatic compounds in an amount of from 15% or less by weight of the feedstock. In certain embodiments, the $C_{9+}$ aromatic compounds may be present in the feedstock in any amount range within the amounts of 0.1%, 0.2%, 0.5%, 1%, 2%, 3%, 4%, 5%, 6%, 7%, 8%, 9%, 10%, or 15% by weight of the feedstock.

Further, the benzene-depleted feedstock or feed may contain non-aromatic compounds in an amount of from 10% or less by weight of the feedstock. In certain embodiments, the non-aromatic compounds may be present in any amount range within the amounts of 0.1%, 0.2%, 0.5%, 1%, 2%, 3%, 4%, 5%, 6%, 7%, 8%, 9%, or 10% by weight of the feedstock.

It should be understood, however, that the present invention has applicability to benzene-depleted aromatic feedstocks having benzene, toluene, xylene, ethylbenzene and $C_{9+}$ aromatics at levels other than those expressly recited.

In accordance with the present invention, an aromatic-containing product or feedstock, which may be a benzene-depleted product or feedstock, is further processed by contacting at least a portion of such product or feedstock with either a xylene-selective catalyst and/or a benzene-selective catalyst to produce xylene and/or benzene products, respectively.

As used herein, a "xylene-selective catalyst" is meant to encompass those catalysts that are active and selective for toluene alkylation, for example toluene alkylation with methanol. The xylene-selective catalyst may be a catalyst that is effective increasing production of xylene when used in toluene methylation, and which results in the methylation of toluene present in the aromatic-containing hydrocarbon feed.

In certain embodiments, the xylene-selective catalyst may be a para-selective catalyst that results in an increased production of para-xylene relative to the other xylene isomers. Para-xylene tends to be more highly valued than the other xylene isomers. Such xylene-selective catalysts are often zeolite catalysts, particularly medium pore zeolites, such as ZSM-5 zeolite. Non-limiting examples of suitable xylene-selective catalysts, which may also be para-selective, may include those described in U.S. Pat. Nos. 7,060,864; 7,084,318; 7,105,713; 7,196,237; 7,244,869; 7,279,608; 7,285,511; 7,304,194; 7,368,410; 7,399,727; 7,446,069; 7,507,685; 7,560,608; 7,576,026; 7,629,498; 7,625,793; 7,662,737; 7,674,942; 7,713,898; 8,062,987; and 8,115,041, each of which is incorporated herein by reference in its entirety for all purposes.

In particular embodiments, the xylene-selective catalyst is a phosphorus-containing zeolite, which may be a medium pore zeolite such as a ZSM-5 zeolite, that is bound with an inorganic binder and has at least two $^{31}$P MAS NMR peaks with maxima at from 0 ppm to −55 ppm, with at least one $^{31}$P MAS NMR peak having a maximum at from −40 ppm to −50 ppm. Such catalysts, their preparation, and use are described in detail in U.S. Pat. Nos. 7,368,410; 7,507,685; and 7,674,942, which have each been incorporated herein by reference.

In certain cases, the xylene-selective catalyst may be formed by particular preparation techniques. In such methods, a zeolite is modified by treating the zeolite with a phosphorus-containing compound. The zeolite may be a medium pore zeolite, such as a ZSM-5 zeolite. The zeolite may include those having a $SiO_2/Al_2O_3$ molar ratio of 25, 50, 100, 200 or higher, more particularly from about 200 to about 500, prior to modification. The starting ZSM-5 zeolite may be an $NH_4^+$ or $H^+$ form and may contain traces of other cations.

The phosphorus-containing compounds may include, but are not limited to, phosphonic, phosphinous, phosphorus and phosphoric acids, salts and esters of such acids and phosphorous halides. In particular, phosphoric acid ($H_3PO_4$), ammonium dihydrogen phosphate ($NH_4H_2PO_4$) and ammonium hydrogen phosphate (($NH_4)_2HPO_4$) may be used as the phosphorus-containing compound to provide a catalyst for toluene methylation with shape selective properties to provide increased p-xylene selectivity. Such modified catalysts may contain phosphorus (P) in an amount of from about 0.01 to about 0.15 g P/g zeolite, more particularly from about 0.02 to about 0.13 g P/g zeolite, and more particularly from about 0.07 g P/g zeolite to about 0.12 g P/g zeolite, and still more particularly from about 0.09 g P/g zeolite to about 0.11 g P/g zeolite. After phosphorus treatment, the phosphorus-treated zeolite may be dried.

The phosphorus-modified zeolite is then heated. By heating at temperatures of 300° C. or higher after phosphorus treatment this may result in the formation of various phosphorus species within the zeolite. Such heating may also facilitate drying of the catalyst after the phosphorus treatment. Temperatures of 300° C., 400° C. or more are particularly useful in providing such increased para-selectivity. A suitable range for such heating subsequent to phosphorus treatment is from about 300° C. to about 600° C. Such heating may be carried out for 0.5 hour or more.

After the heating step, as discussed above, the phosphorus-modified zeolite is then bound with a suitable binder. Suitable binder materials may include inorganic oxide materials. Examples of such materials include alumina, clay, aluminum phosphate, silica and silica-alumina. In particular, a binder of alumina, silica-alumina or clay or their combinations are particularly useful. The bound catalyst may contain from about 1% to about 99% by total weight of bound catalyst, more particularly from about 10% to about 50% binder by total weight of bound catalyst.

To form the bound catalyst, the binder material may be combined with the phosphorus-modified zeolite to form an extrudable mixture. After binding, the phosphorus-modified zeolite bound with the binder may be calcined or heated at a temperature of 400° C. or higher, more particularly at a temperature between 500° C. and 700° C. Such heating may be carried out for 0.5 hours or more to form the bound catalyst. It has been discovered that heating the P-treated ZSM-5 at a temperature of about 300° C. or higher and then binding the zeolite with a suitable binder, as described herein, may result in the bound zeolite exhibiting multiple P-species, as shown by $^{31}P$ MAS NMR peaks.

The xylene-selective catalysts, as described, can be used in toluene methylation reactions to produce xylene from the hydrocarbon feeds, including benzene-depleted feedstocks and other feedstocks containing toluene under alkylation reaction conditions. Such conditions include toluene-to-methanol molar ratios of from 1 or higher, reactor pressures ranging from atmospheric to 20 psig, 50 psig, 100 psig, 200 psig or higher, and reaction temperatures of from 400° C. or higher. The feed may contain steam and/or a diluting agent, such as $H_2$ or any other inert gas or gases.

As used herein, a "benzene-selective catalyst" is meant to encompass those catalysts that result in the dealkylaton of alkylated aromatic compounds, such as toluene, xylene, ethylbenzene, and $C_{9+}$ aromatics, to form benzene under dealkylation reaction conditions. The catalyst may contain disproportionation catalytic properties for toluene or other aromatic to produce benzene and dialkylated aromatics. The benzene-selective catalyst may be that that results in increased production of benzene when used in dealkylation of mono-alkylated aromatic compound.

An example of benzene-selective catalysts are those catalysts described in U.S. application Ser. No. 13/540,022, filed Jul. 2, 2012, the disclosure of which is herein incorporated by reference in its entirety for all purposes.

In particular embodiments, the benzene-selective catalyst is a phosphorus-containing zeolite having a phosphorus content of 7.5% or less by weight of zeolite and a $^{27}Al$ MAS NMR peak at 50 ppm that is greater than any other $^{27}Al$ MAS NMR peak and that has a pore volume of about 0.2 ml/g or more. In particular embodiments, the phosphorus-containing zeolite forming the benzene-selective catalyst may have a phosphorus content of from 0.1% to 4.5% by weight of the zeolite. In other embodiments the phosphorus content of the zeolite will be from 0.1 to 2% or 3% by weight of the zeolite. Such benzene-selective catalysts may be formed from a pentasil zeolite containing 10-membered ring pore openings, such as a ZSM-5 zeolite. In some embodiments, the zeolite may have a $SiO_2/Al_2O_3$ molar ratio of at least 25 or more. In still other embodiments, the zeolite may have a $SiO_2/Al_2O_3$ molar ratio of at least 200 or more. In some embodiments, the zeolite may be a silicalite having little or no aluminum in the zeolite framework.

In certain cases, the benzene-selective catalyst may be formed by particular preparation techniques. Such preparation techniques may result in the formation of benzene-selective catalyst having the above-discussed $^{27}Al$ MAS NMR peak, phosphorus content, and pore volume. In such techniques, the benzene-selective catalyst is formed from a pentasil zeolite, such as a ZSM-5 zeolite, that is modified by treating it with phosphorus-containing compounds. The zeolite may have a $SiO_2/Al_2O_3$ molar ratio of from about 25 or higher, more particularly from about 25 to about 1000 or higher prior to modification, more particularly, the $SiO_2/Al_2O_3$ molar ratio may be from about 25, 30, 50, 80, 100, 200, 250, 280, 300, 350, 400, 500 to about 1000 or more, including any and all data points within such range and the end points of such range. In certain applications, the ZSM-5 zeolite may have a $SiO_2/Al_2O_3$ molar ratio of from about 200 or more, and still more particularly from about 200 to about 400 or more, prior to modification. The starting ZSM-5 zeolite may be an $NH_4^+$ or $H^+$ form and may contain traces of other cations.

The phosphorus-containing compounds used to treat the zeolite may include, but are not limited to, phosphonic, phosphinous, phosphorus and phosphoric acids, salts and esters of such acids and phosphorous halides. In particular, phosphoric acid ($H_3PO_4$), ammonium dihydrogen phosphate ($NH_4H_2PO_4$), and ammonium hydrogen phosphate (($NH_4)_2HPO_4$) may be used as the phosphorus-containing compound. Such phosphorus-treated catalysts may contain phosphorus (P) in an amount of from about 1 wt % to about 25 wt % or more by weight of the zeolite after the phosphorus treatment. In certain embodiments, the phosphorus content may be from about 5 wt % to 15 wt % or more by weight of the zeolite after phosphorus treatment. In other embodiments, the phosphorus content may be from about 7 wt % to 12 wt % by weight of the zeolite after phosphorus treatment.

The phosphorus treatment used in forming the benzene-selective catalyst may be carried out by various techniques. This may include aqueous phosphorus treatment of the zeolite. The treatment may include slurry evaporation, wet incipient and spray-dry methods. Solid-solid mixing of the zeolite and a phosphorus compound followed by bringing the mixture in contact with water as a liquid or vapor phase may also be used.

In slurry evaporation, the phosphorus may be incorporated into the catalyst by preparing a slurry of the zeolite and an aqueous solution of the phosphorus compound. Heating of the slurry may be used to facilitate treatment of the zeolite and to evaporate liquids. Heating of the slurry to temperatures of from about 25° C. or more, with from about 70° C. to about 100° C. being suitable in most instances. The slurry may also be stirred or agitated during this step to ensure uniform treatment. Heating the zeolite slurry to near complete evaporation of the liquid causes the formation of dough which can be dried or calcined to form powder or particles. The evaporation of the liquid from the zeolite slurry can be alternatively achieved by using a spray-dry technique.

In the wet incipient method, an aqueous solution of the phosphorus compound is added, such as by spraying, to dry zeolite without forming a slurry. The dry zeolite, which may be initially in the form of a powder, may be mixed with the phosphorus compound or its aqueous solution. If necessary, water may be added to the mixture of zeolite powder and phosphorus containing compound or its solution to facilitate homogeneous or uniform interaction between them.

The unbound phosphorus-treated zeolite used to form the benzene-selective catalyst is then calcined at a temperature of about 250° C. or more, more particularly, a temperature from about 300° C. to about 700° C., and more particularly from about 400° C. to about 600° C., in an environment containing oxygen, typically air. Calcining may take place over time, typically from several minutes to one hour or more. Calcining may also take place by gradually increasing the temperature over time.

After calcination, the zeolite may optionally undergo a steaming step using superheated steam (i.e., dry steam or steam with no liquid water present). As used herein with respect to the benzene-selective catalyst, the expressions "steaming," "steamed," and similar expressions are meant to refer to the contacting of the zeolite with such superheated steam and are to be distinguished from the water treatment(s) discussed later on unless expressly stated so or as may be otherwise apparent from the context. The catalyst may be steamed at a temperature of 200° C. or more, more particularly at a temperature of from about 200° C. to about 600° C. or higher. Pressures during steaming may typically range from atmospheric to about 50 psig (344.7 kPa) or 100 psig or more. Steaming may be carried out from a few minutes to several hours. The steaming may occur in the presence of hydrogen gas ($H_2$), air or other inert gas flow. In other embodiments no steaming may be conducted after calcinations and prior to the water treatment as will now be discussed.

The unbound phosphorus-treated calcined zeolite powder, with or without steaming, is modified using a water treatment that alters the characteristics and properties of the phosphorus-containing zeolite to form the benzene-selective catalyst. The water treatment is carried out by contacting the calcined phosphorus-treated zeolite powder with liquid water. This may be in the form of liquid water or a stream containing essentially wet or liquid water. This may include saturated steam or a mixture of liquid water and a gas, such as water and hydrogen gas. Accordingly, as used herein, the expression "water treatment" and similar expressions are meant to encompass the treatment of the unbound phosphorus-containing zeolite powder with liquid water or a combination or mixture of liquid water and steam or other gas and is to be distinguished from "steaming," as it has been defined and described previously.

In most instances, the water treatment is conducted at a temperature of from above 0° C. to about 100° C., with the pressure conditions being at or around atmospheric pressure conditions or that allow for the presence of some portion of liquid water. There may be other instances, however, where the pressure is below or above atmospheric pressure. In such instances, the liquid water treatment is conducted at a temperature to ensure that the water temperature is at or above the water's freezing point and at or about the boiling point for the particular pressure conditions to ensure that at least a portion (e.g., 1% or more) of the water is in the liquid phase. In many applications, the liquid water treatment is carried out at a temperature of about 25° C. (room temperature) to about 120° C. In certain applications, temperatures of from about 50° C., 60° C. or 70° C. to about 100° C., 110° C. or 120° C. may be used in the water treatment. In certain embodiments, the liquid water treatment may be carried out at a temperature of from about 50 or 60° C. to about 90° C. or 100° C.

The water treatment facilitates the removal of significant amounts of phosphorus from the phosphorus-treated zeolite. In particular, the water treatment should be carried out to facilitate final removal of about 70% by weight or more of phosphorus from the unbound phosphorus-treated zeolite. This amount includes any phosphorus that may be removed by any optional steaming conducted prior to the water treatment. Testing has shown that steaming (i.e., with superheated steam) typically results in less than 20% by weight of phosphorus being removed from the phosphorus-treated zeolite. Thus, steaming alone is insufficient to remove the required amount of phosphorus from the unbound phosphorus-treated zeolite. The water treatment thus facilitates significant amounts of phosphorus being removed from the zeolite. In certain instances, from about 70% to about 90% or more phosphorus is removed from the phosphorus-treated zeolite after the water treatment.

The amount of phosphorus in the zeolite after water treatment will typically be from 7.5% or less by weight of the zeolite. In certain applications, the amount of phosphorus remaining in the zeolite will be from 0.1% to 4.5% by weight of the zeolite. In other embodiments the phosphorus remaining in the zeolite will be from 0.1 to 2% or 3% by weight of the zeolite.

The water treatment also facilitates altering the surface area and pore volume of the unbound phosphorus-treated zeolite. In particular, the water treatment should be carried out in a manner to facilitate an increase of in the pore volume of the zeolite by at least 50% compared to the zeolite prior to the water treatment. In particular embodiments, the pore volume increase may be 50%, 60%, 70%, 80%, 90%, 100%, 110%, 120% or more.

Various methods of the water treatment may be used in forming the benzene-selective catalyst. The water treatment used, however, should be sufficient to provide the properties described herein. In one method of the water treatment, the unbound and calcined phosphorus-treated zeolite, with or without prior steaming, is contacted with a gaseous water treatment wherein the zeolite is contacted with liquid water in a gas stream. In the gaseous water treatment the water may be in the form of saturated steam (i.e., water at boiling point), containing both liquid water and water vapor. The saturated steam may be a pure saturated steam or it may be mixed with other non-water gases. The non-water gases may include hydrogen gas or another gas (e.g., $N_2$, $CO_2$, light alkanes, air, etc.), which may be an inert gas, or combination of such gases.

Alternatively, where the water treatment is carried out below the boiling point of water, the gaseous water treatment may utilize a mixture of liquid water and a non-water gas. Such treatment may be carried out by bubbling or passing flowing hydrogen or other gas through liquid water at conditions above the water's freezing point and below or at the water's boiling point so that some amount of the liquid water is entrained within the flowing gas diluent.

In certain embodiments, the gaseous water treatment may take place during cooling that initially starts as a steam treatment where the zeolite is treated with superheated steam at elevated temperatures in a steaming step, but then the temperature is reduced so that the zeolite is eventually contacted and treated with the liquid water as the steam cools to saturated steam and/or liquid water entrained or mixed with a non-water gas stream. The duration of the gaseous water treatment may range from a few minutes to several hours or even days.

In one method for the water treatment, the water treatment is carried out by mixing or immersing the phosphorus-treated zeolite in a liquid water bath or slurry. The immersion time may vary from a few minutes to several hours or even days. In most embodiments, the immersion time will range from about one hour to several hours or days. The immersion may be carried out with or without agitation of the zeolite within the water bath, with the provision that such immersion technique provides the desired final properties described herein.

In another method, the water treatment includes contacting the phosphorus-treated zeolite in a flowing liquid water stream where the water is at least partially in a liquid phase. This may be done by contacting the zeolite in a forced stream containing liquid water. The flowing liquid water stream may also contain a non-water gas diluent. The duration of the flowing liquid stream may range from a few minutes to several hours or even days. The duration times for the flowing liquid stream without the use of any gas diluents may be the same as those for the water bath or may be shorter.

The removal of large amounts of phosphorus from the phosphorus-treated zeolite and the increase in pore volume provided by the water treatments described herein is likely due to the removal of various phosphorus species (hereinafter called debris) from the zeolite channels. Such debris may include occluded phosphates, phosphates bonded with non-framework aluminum and silicon, and amorphous alumina.

In addition to the removal of phosphorus and increase in surface area and pore volume of the zeolite, the water treatment also results in a significant change in zeolite framework aluminum (Al). This has been confirmed by an exhibited increase in the $^{27}$Al MAS NMR peak intensity at 50 ppm, which is assigned to tetrahedral or framework aluminum of the zeolite. This has been described more fully in copending U.S. application Ser. No. 13/540,022. Dealumination or a loss of framework or tetrahedral aluminum, which is shown by a decrease in the $^{27}$Al MAS NMR peak intensity at 50 ppm, typically results from the phosphorus treatment and calcinations of the zeolite. The water treatment described herein results in an increase in $^{27}$Al MAS NMR peak intensity at 50 ppm, as well as a decrease or disappearance of a strong (doublet)$^{27}$Al MAS NMR peak between −10 ppm and −20 ppm that is assigned to octahedral aluminum (non-framework Al). Thus, there is an increase in the ratio of the $^{27}$Al MAS NMR peak intensity at 50 ppm to total aluminum provided by the water treatment. The increased $^{27}$Al MAS NMR peak at 50 ppm due to the water treatment may be greater than any other $^{27}$Al MAS NMR peak within the spectrum.

Furthermore, the increase of tetrahedral Al peak (showing $^{27}$Al MAS NMR peak at 50 ppm) occurs without the addition of additional reactants or modifying agents. In forming the benzene-selective catalyst, the water treatment may be at acidic or conditions where the pH is from 7 or below, with the lower pH being caused by phosphorus or loosely bound phosphates from the phosphorus treatment, which may make the water used during the water treatment acidic. No added bases (e.g., KOH, NaOH, etc.), acids (e.g., HCl, acetic acid, benzoic acid, $H_2SO_4$, nitric acid, mineral acids, etc.), ammonium salts or compounds, added aluminum compounds (e.g., $Al(NO_3)_3$, $Al_2(SO_4)_3$, etc.) or other reactants or modifying agents are needed or may be used during the water treatment.

After the water treatment, any residual water may be separated from the zeolite, such as through filtration, decantation, etc. Further heating to dry the zeolite after the water treatment may also be carried out. Typical drying temperatures may range from about 70° C. to 120° C. and higher.

An additional calcination step may also be employed after the water treatment using the calcination temperatures and times previously discussed.

The water treated phosphorus-modified zeolite can be used as a benzene-selective catalyst, and may be optionally bound with a binder to form into a shaped catalyst. The binder materials may include inorganic oxide materials, such as alumina, clay and silica materials. The binder may be used to provide a desired shape to the catalyst, for example, 1/16-inch cylindrical shaped extruded catalyst. In particular, a binder of an aluminum-containing material, such as alumina, clay, aluminum phosphate, silica-alumina or other-aluminum containing material, or their combinations, may be particularly useful. The bound catalyst may contain from about 1 wt % to about 99 wt % of binder material by total weight of the catalyst. In some applications the binder may be present in an amount of from about 10 wt % to about 50 wt % binder by total weight of catalyst.

The water-treated phosphorus-containing zeolite, bound or unbound, may also undergo a further steaming step prior to the initial use as a catalyst. The catalyst may be steamed at a temperature of between 200 and 600° C. or higher before using the catalyst in any reaction. The steaming can be carried out in-situ or ex-situ of the reactor. In other embodiments no further steaming may be conducted after the water treatment.

After drying and/or calcinations and any further steam treatment, the water-treated, phosphorus-containing zeolite, prepared and as described above, may be used as a benzene-selective catalyst in the methods described herein.

The following discussion relates to how the benzene-selective and xylene-selective catalysts can be used in various systems and hydrocarbon conversion methods.

Referring to FIG. 1, a flow schematic of a System A that may be used for the conversion of hydrocarbons in accordance with the invention is shown. In the embodiment shown, the conversion System A includes a hydrocarbon processing unit 12 wherein a hydrocarbon feed 14 is fed to the unit 12. The unit 12 in certain embodiments may be a thermal cracking unit, such as a steam cracking unit typically used for steam cracking of naphtha, gas oil or other petroleum feedstocks. The unit 12 may be representative of any processing unit(s) or system(s) that produces hydrocarbon products that may contain benzene and at least one of toluene, $C_8$ aromatics, and $C_{9+}$ aromatics. Thus, the unit 12 may include a cracking unit or units, as well as distillation columns, separation equipment, etc. The feed 14 may be a full range naphtha or a heavy naphtha feed (i.e., typically those hydrocarbons having boiling point of from 90° C. to 200° C.) or a portion of the feed may be composed of a heavy naphtha. Such heavy naphtha feed is typically composed of aromatic hydrocarbons. The feed 14 may be provided from a variety of refinery products, such as used in olefin production and refining of crude oil, and may have undergone various refinery processes or processing steps prior to introduction into the unit 12. Additionally, other feeds or cofeeds that facilitate the production of hydrocarbon products containing benzene and the at least one of toluene, $C_8$ aromatics, and $C_{9+}$ aromatics may be supplied to the unit 12 but are not shown.

The unit 12 may be operated at those conditions and severity suitable or conducive to the production of benzene, which may be removed from the unit 12 as a petroleum gasoline or pygas product stream 16 that contains naphtha cracking products of olefins and aromatics. The pygas product stream 16 may be introduced into a separation or extraction unit 18, which may be in the form of a distillation column or other separation device, operated at conditions suitable for the separation of benzene. A benzene product stream 20 is removed and separated from a benzene-depleted product stream 22 containing alkylated aromatics. The benzene-depleted product stream 22 has a composition similar to those benzene-depleted products previously discussed.

The benzene-depleted product stream 22 is introduced as a feed to one or more reactor units 24 having a catalyst bed(s) 26 containing a benzene-selective catalyst. The benzene-selective catalyst may include any of those previously described. The reactor unit 24 is operated at conditions suitable described earlier for the conversion of alkylated aromatic compounds into benzene. The aromatic compound(s) containing alkylated aromatics contacts the benzene-selective catalyst within the reactor 24 to facilitate conversion of the aromatic compounds into benzene.

The effluent 28 from reactor unit 24, which is a benzene-enriched output stream, may be directed to a separator or extraction unit 30, which may be in the form of a distillation column, that is operated at conditions suitable for the separation of benzene from other products. A benzene product stream 32 is removed from the unit 30 with the remainder forming an output stream 34. The benzene product 32 may be combined with the benzene product 20 to form benzene-product stream 36. Alternatively, all or a portion of the product stream 32 may be directed elsewhere.

The output stream 34 contains alkylated aromatics, such as toluene, etc., and may then be introduced into one or more reactor units 40 having a catalyst bed(s) 42 containing a xylene-selective catalyst. Stream 38 containing methanol or other methylating or alkylating agent is added to reactor unit 40 either by adding with stream 34 or by adding directly to unit 40. The xylene-selective catalyst may include any of those previously described and may be a para-xylene selective catalyst in certain embodiments. The separator output stream 34 plus stream 38 contacts the xylene-selective catalyst 42 within the reactor 40 to facilitate conversion of aromatic compounds into xylene. The reactor unit 40 is operated at conditions suitable for the conversion of aromatic compound(s) of the separated product 34 containing toluene and an alkylating agent, such as methanol, into xylene. In certain applications, para-xylene may be produced in larger quantities where such reaction conditions and catalyst are suitable for the production of para-xylene. Steam and $H_2$ or other inert gas or gases may optionally be added to reactor unit 40 to provide improved catalyst performance or improved catalyst stability.

The reactor effluent 44 from reactor unit 40 may be directed to a separator or extraction unit or units (not shown in FIG. 1) in the form of distillation columns that are operated at conditions suitable for the separation of $H_2$, light hydrocarbons, aqueous fluids and oxygenates. The separated streams of $H_2$, $H_2O$ and oxygenate may be recycled to reactor unit 40.

Stream 44, after separation of $H_2$, light hydrocarbons, $H_2O$ and oxygenates, may be directed to a separator or extraction unit 46, which may be in the form of a distillation column, that is operated at conditions suitable for the separation of (unconverted) toluene, ethylbenzene, mixed xylene and $C_{9+}$ hydrocarbons. A toluene-rich stream 48 from separation unit 46 may then be recycled to unit 40 and/or unit 24. Separated stream 50 from separator 46 is directed to a separator or extraction unit 52, which may be in the form of a distillation column, that is operated at conditions suitable for the separation of mixed xylene and $C_{9+}$ hydrocarbons. Stream 54 containing mixed xylenes may further be processed to separate p-xylene by known technology (e.g., crystallization, adsorption).

Stream 54 may contain ethylbenzene, which after separation from xylene (e.g., by distillation, etc.) may also be recycled to unit 24 (not shown in FIG. 1). Stream 56 contains $C_{9+}$ aromatic hydrocarbons. All or a portion of stream 56 from separation unit 52 may be recycled to reactor unit 40 or it may directed elsewhere as product stream 56 for further processing, storage, or use.

The sequence or order of reactor units 24 and 40 with the catalysts described herein and the respective separation units can be alternated, with reactor 40 being located upstream from reactor 24, with appropriate adjustment or modification. The use of reactor unit 40 for the production of xylene can also be eliminated if xylene products are not wanted or are need to be minimized.

The following examples serve to further illustrate the invention.

EXAMPLES

Catalyst Preparation

Catalysts A-C

Catalysts A-C constitute xylene-selective catalysts. Catalysts A, B and C were phosphorus modified ZSM-5 (P/ZSM-5) formed catalysts and were prepared by treating $NH_4$-ZSM-5 zeolite powder having a $SiO_2/Al_2O_3$ molar ratio between 282 and 308 with the P-containing compound ($H_3PO_4$) by using a wet-incipient method and then heating to a maximum temperature between 500° C. and 550° C. to form a P/ZSM-5 zeolite catalyst powder. The catalyst powder was formed into a shaped catalyst by binding with about 20% alumina as binder and extruded to make a 1/16-inch cylindrical shaped extruded catalyst. The extruded catalyst was calcined or heated at a maximum temperature between 500° C. and 550° C. for about 5 hours. The catalysts were analyzed for Si, Al and P by XRF technique and for BET surface area (SA) and total pore volume (PV) by $N_2$ adsorption and are shown in Table 1.

Catalysts D-F

Catalysts D, E and F constitute benzene-selective catalysts. Catalysts D, E and F were phosphorus modified ZSM-5 (P/ZSM-5) formed catalyst and were prepared by treating $NH_4$-ZSM-5 zeolite powder. Prior to the P-treatment, ZSM-5 zeolite used for Catalysts D and F had $SiO_2/Al_2O_3$ molar ratios of 358 and for Catalyst E had a $SiO_2/Al_2O_3$ molar ratio of 302. Each zeolite was treated with P-containing compound ($H_3PO_4$) by using a wet-incipient method and then heated at a maximum temperature of between 500° C. and 550° C. to form a P/ZSM-5 zeolite catalyst powder. The catalyst powder was then treated with water in a water treatment by making a slurry of the P/ZSM-5 powder with liquid water and heating the slurry at about 100° C. for about 4 hours. The slurry was filtered and dried at 110° C. The treatment of the P/ZSM-5 with water resulted in a significant decrease of phosphorus content and an increase in pore volume of the powder catalyst. The powder catalyst was formed into a shaped catalyst by binding with 20% alumina as binder and extruded to form $\frac{1}{16}$-inch cylindrical shaped extruded catalyst. The extruded catalyst was calcined or heated at a maximum temperature between 500° C. and 550° C. for about 10 h. The catalysts were analyzed for Si, Al and P by XRF technique and for BET surface area (SA) and total pore volume (PV) by $N_2$ adsorption and are shown in Table 1.

TABLE 1

| Catalyst | Elemental Analysis, wt % | | | $N_2$ Adsorption | |
|---|---|---|---|---|---|
| | $SiO_2$ | $Al_2O_3$ | P | SA, $m^2/g$ | PV, cc/g |
| Powder Catalyst A | 77.79 | 0.53 | 8.53 | 211 | 0.13 |
| Extruded Catalyst A | 63.49 | 18.44 | 7.09 | 243 | 0.17 |
| Powder Catalyst B | 77.05 | 0.44 | 9.11 | 182 | 0.12 |
| Extruded Catalyst B | 63.47 | 18.54 | 7.44 | 209 | 0.18 |
| Powder Catalyst C | 76.59 | 0.59 | 8.67 | 199 | 0.13 |
| Extruded Catalyst C | 62.79 | 18.66 | 7.02 | 245 | 0.17 |
| P/ZSM-5 Powder | 78.11 | 0.47 | 7.69 | 199 | 0.14 |
| Powder Catalyst D | 98.06 | 0.49 | 0.56 | 323 | 0.27 |
| Extruded Catalyst D | 78.45 | 20.91 | 0.44 | 300 | 0.29 |
| P/ZSM-5 Powder | 76.59 | 0.59 | 8.67 | 199 | 0.13 |
| Powder Catalyst E | 91.41 | 0.57 | 2.80 | 277 | 0.25 |
| Extruded Catalyst E | 75.15 | 20.80 | 1.89 | 287 | 0.26 |
| P/ZSM-5 Powder | 80.04 | 0.45 | 7.83 | 200 | 0.13 |
| Powder Catalyst F | 90.15 | 0.49 | 3.43 | 240 | 0.20 |
| Extruded Catalyst F | 69.66 | 25.05 | 1.30 | 283 | 0.27 |

Figure 2:
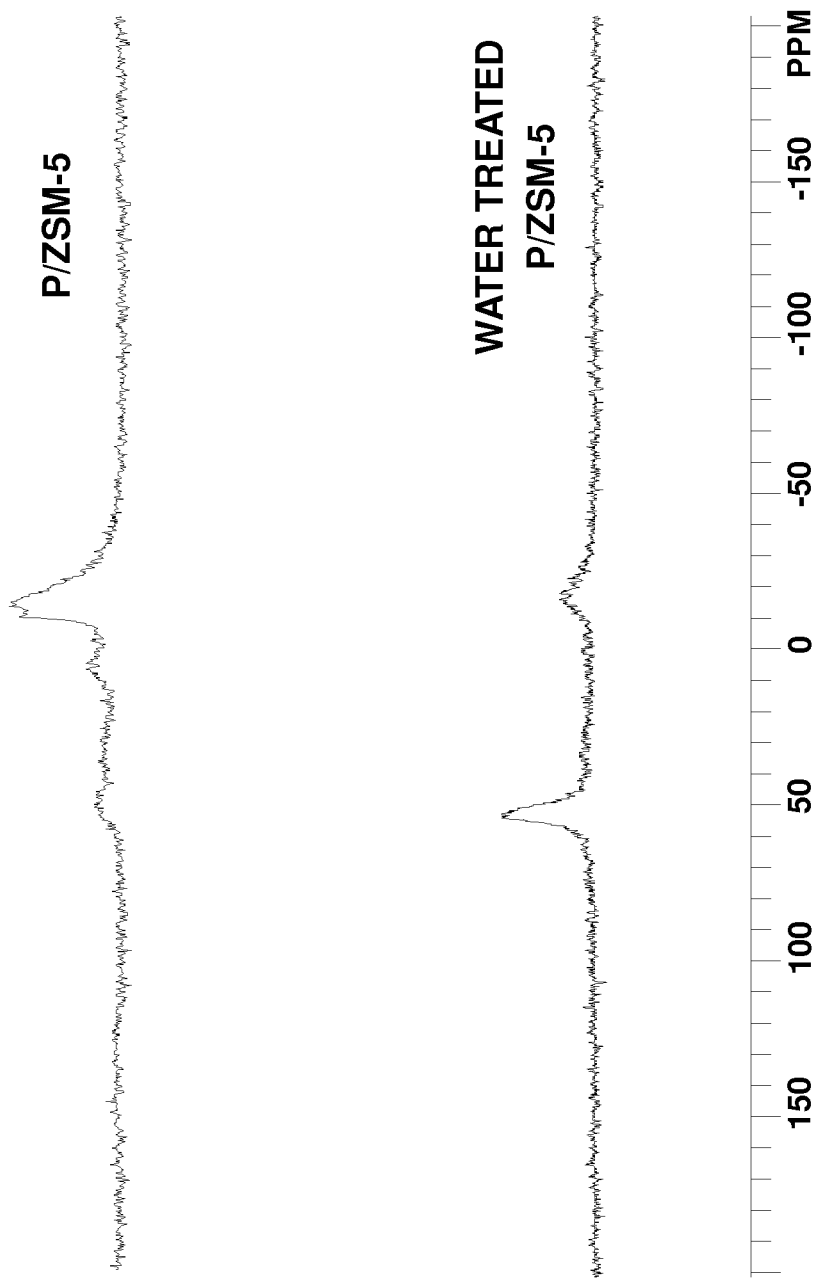
FIG. 2 shows a plot of $^{27}Al$ MAS NMR spectra for a phosphorus-modified ZSM-5 (P/ZSM-5) zeolite and the same P/ZSM-5 zeolite that has been subjected to a water treatment.

Although the particular catalyst materials were not used in conversion of aromatic hydrocarbons the example is given here to show the characteristic of $^{27}Al$ MAS NMR peaks before and after the water treatment described above. A P-treated ZSM-5 zeolite (powder catalyst B) was treated with water at about 100° C. as described above for Catalyst D, E or F. The water treated catalyst contained 80.04 wt % $SiO_2$, 0.49 wt % $Al_2O_3$, 1.05 wt % P, and had a BET surface area of 305 $m^2/g$ and a total pore volume of 0.256 ml/g. FIG. 2 shows $^{27}Al$ MAS NMR spectra of a P-treated ZSM-5 zeolite powder without water treatment and a water treated P/ZSM-5 zeolite powder. The Al peak at or near 50 ppm reappeared or increased after the water treatment.

Example 1-2

Catalyst A was tested with a benzene-depleted pygas stream (obtained from a cracker plant) at two different conditions. The benzene depleted pygas stream contained 3.31 wt % benzene, 0.11 wt % methyl cyclohexane, 1.24 wt % n-heptane, 53.52 wt % toluene, 1.17 wt % n-octane, 10.67 wt % ethylbenzene, 3.11 wt % p-xylene, 8.59 wt % m-xylene, 5.28 wt % o-xylene, 9.26 wt % $C_{9+}$ aromatics, and 3.75 wt % hydrocarbons that were not identified by the analytical method used. The reaction was carried out in a stainless steel tubular reactor in a down-flow mode under conditions suitable for alkylation. A fixed volume of sized (20-40 mesh) catalyst was loaded in the reactor, dried at 200° C. under $H_2$ flow for about 1 hour, steamed at 200° C. overnight under the flow of steam and $H_2$, and then introduced the aromatic feed mixed with methanol; $H_2$ and steam were added as cofeed. The catalyst bed temperature was ramped to the desired reaction temperature and once the reactor reached steady state conditions the reactor product streams were analyzed. The reaction conditions and analyses for feed and product streams are presented in Table 2.

TABLE 2

| EXAMPLE | 1 | | 2 | |
|---|---|---|---|---|
| Catalyst | A | | A | |
| Catalyst load, g | 4.70 | | 4.70 | |
| Catalyst volume, ml | 5.7 | | 5.7 | |
| Feed Rate | 2.05 | | 1.96 | |
| Aromatics, g/min | 0.1611 | | 0.1541 | |
| Methanol, g/min | 0.0042 | | 0.0077 | |
| H2 (Cofeed gas), cc/min | 420 | | 420 | |
| H2O as steam, g/min | 0.0295 | | 0.0294 | |
| LHSV* | 2.05 | | 2.00 | |
| Reactor Inlet Pressure, psig | 20.5 | | 20 | |
| Average Catalyst Bed Temp/° C. | 505.5 | | 556 | |
| | Hours on stream | | | |
| | 120 | | 55 | |
| Stream Name | Feed | Product | Feed | Product |
| Stream Analysis, wt % | | | | |
| H2 | 14.78 | 15.21 | 15.33 | 15.48 |
| C1-C5 Nonaromatics | 0 | 1.51 | 0 | 1.90 |
| Water | 13.25 | 15.42 | 13.62 | 16.11 |
| Methanol | 1.87 | 0.73 | 3.59 | 1.31 |
| Benzene | 2.32 | 2.14 | 2.22 | 1.99 |
| Methyl-Cyclohexane | 0.08 | 0.7 | 1.00 | 0.69 |
| Heptane | 0.87 | 0.41 | 0.38 | 0.30 |
| Toluene | 37.53 | 33.76 | 35.52 | 29.78 |
| Octane | 0.82 | 0.65 | 1.32 | 0.82 |
| Ethyl benzene | 7.48 | 6.85 | 7.06 | 6.31 |
| p-Xylene | 2.18 | 4.62 | 2.06 | 7.32 |
| m-xylene | 6.02 | 6.01 | 5.68 | 6.00 |
| o-Xylene | 3.70 | 3.74 | 3.50 | 3.74 |
| C9+ | 6.49 | 6.59 | 6.21 | 6.91 |
| Unknown | 2.63 | 1.66 | 2.51 | 1.35 |
| Conversion, wt % | | | | |
| Methanol | | 59.75 | | 62.85 |
| Benzene | | 5.40 | | 8.82 |
| Toluene | | 7.85 | | 14.71 |
| Ethyl benzene | | 6.14 | | 9.00 |
| Selectivity, wt % in Aromatics Products Formed | | | | |
| Mixed-Xylene Formed | | 91.6 | | 88.2 |
| C9+ Formed | | 8.4 | | 11.8 |
| p-X (formed) in formed mixed-xylene | | 90.2 | | 88.3 |
| Aromatic ring balance, % | | 98.7 | | 99.8 |

*LHSV based on aromatics + methanol feed

Examples 3-4

A blended feed was made containing $C_7$, $C_8$ and $C_9$ aromatics for conversion over catalysts B and C, which were described earlier. The blended feed contained 3.31 wt % benzene, 0.11 wt % methyl cyclohexane, 1.24 wt % n-heptane, 57.34-57.38 wt % toluene, 1.17 wt % n-octane, 10.58-10.64 wt % ethylbenzene, 3.11 wt % p-xylene, 8.54 wt % m-xylene, 5.26-5.28 wt % o-xylene, 9.27 wt % $C_{9+}$ aromatics. The reaction was carried out in a reactor described in Example 1. The reaction conditions and analyses for feed and product streams are given in Table 3.

TABLE 3

| EXAMPLE | 3 | 4 |
|---|---|---|
| Catalyst | B | C |
| Catalyst load, g | 3.88 | 3.64 |
| Catalyst volume, ml | 5.40 | 5.40 |
| Feed Rate | | |
| Aromatics, g/min | 0.3125 | 0.3130 |
| Methanol, g/min | 0.0083 | 0.0083 |
| H2 (Cofeed gas), cc/min | 790 | 790 |
| H2O as steam, g/min | 0.062 | 0.0624 |
| LHSV* | 4.07 | 4.08 |
| Reactor Inlet Pressure, psig | 21 | 20 |
| Average Catalyst Bed Temp/° C. | 514 | 555 |

| | Hours on stream | | | |
|---|---|---|---|---|
| | 24 | | 49 | |
| Stream Name | Feed | Product | Feed | Product |
| Stream Analysis, wt % | | | | |
| H2 | 14.07 | 14.46 | 14.02 | 14.50 |
| C1-C5 Nonaromatics | 0 | 0.47 | 0 | 0.68 |
| Water | 13.94 | 15.00 | 14.00 | 14.99 |
| Methanol | 1.86 | 0 | 1.86 | 0 |
| Benzene | 2.32 | 2.54 | 2.32 | 2.82 |
| Methyl-Cyclohexane | 0.08 | 0 | 0.08 | 0 |
| Heptane | 0.87 | 0 | 0.87 | 0 |
| Toluene | 40.22 | 37.44 | 40.21 | 37.02 |
| Octane | 0.82 | 1.00 | 0.82 | 1.02 |
| Ethyl benzene | 7.42 | 6.06 | 7.46 | 5.61 |
| p-Xylene | 2.18 | 6.37 | 2.18 | 6.63 |
| m-xylene | 5.99 | 6.32 | 5.99 | 6.41 |
| o-Xylene | 3.70 | 3.65 | 3.69 | 3.66 |
| C9+ | 6.50 | 6.70 | 6.50 | 6.65 |
| Conversion, wt % | | | | |
| Methanol | | 100 | | 100 |
| Benzene | | — | | — |
| Toluene | | 6.61 | | 7.69 |
| Ethyl benzene | | 18.64 | | 24.65 |
| Selectivity, wt % in Aromatics Products Formed | | | | |
| Benzene Formed | | 4.8 | | 10.0 |
| Mixed-Xylene Formed | | 90.9 | | 87.71 |
| C9+ Formed | | 3.1 | | 2.3 |
| p-X (formed) in formed mixed-xylene | | 93.0 | | 91.35 |
| Aromatic ring balance, % | | 100.8 | | 100.5 |

*LHSV based on aromatics + methanol feed

In Examples 1-4, when using a benzene depleted pygas, Catalysts A, B and C were shown to produce mixed xylenes with greater than 85% mixed-xylene based on aromatics formed (taking into account that the feed contained mixed-xylene). Para-xylene in the produced mixed-xylene product was about 90% or higher.

Example 5-8

Similar to feed of Examples 3-4, benzene-depleted blended feeds were made containing $C_7$, $C_8$ and $C_{9+}$ aromatics and other hydrocarbons for conversion using benzene-selective Catalysts D, E and F, described earlier. The blended feed contained 3.50-3.51 wt % benzene, 58.06-56.07 wt % toluene, 11.55 wt % ethyl benzene, 3.35-3.36 wt % p-xylene, 9.31 wt % m-xylene, 5.68-5.69 wt % o-xylene, 8.53-8.54 wt % $C_{9+}$ aromatics. The reaction was carried out in a reactor as described in Example 1. The reaction conditions and analyses of feed and product streams are given in Tables 4-5 below.

TABLE 4

| EXAMPLE | 5 | 6 |
|---|---|---|
| Catalyst | D | D |
| Catalyst load, ml | 5.40 | 5.40 |
| Catalyst load, g | 3.58 | 3.41 |
| Feed Rate | | |
| Aromatics, g/min | 0.3244 | 0.1597 |
| Methanol, g/min | 0.0089 | 0.0044 |
| H2 (Cofeed gas), cc/min | 790 | 420 |
| H2O as steam, g/min | 0.0620 | 0.0311 |
| LHSV* | 4.23 | 2.08 |
| Reactor Inlet Pressure, psig | 20 | 21 |
| Average Catalyst Bed Temp/° C. | 555 | 552 |

| | Hours on stream | | | |
|---|---|---|---|---|
| | 47 | | 48 | |
| Stream Name | Feed | Product | Feed | Product |
| Stream Analysis, wt % | | | | |
| H2 | 13.59 | 14.06 | 14.59 | 15.01 |
| C1-C5 Nonaromatics | 0 | 2.64 | 0 | 2.96 |
| Water | 13.55 | 14.98 | 13.61 | 14.54 |
| Methanol | 1.94 | 0 | 1.91 | 0 |
| Benzene | 2.48 | 7.19 | 2.45 | 8.07 |
| Heptane | 0 | 0 | 0 | 0 |
| Toluene | 41.18 | 37.19 | 40.59 | 36.19 |
| Ethyl benzene | 8.19 | 1.26 | 8.07 | 4.15 |
| p-Xylene | 2.38 | 5.55 | 2.34 | 7.97 |
| m-xylene | 6.60 | 7.03 | 6.51 | 4.30 |
| o-Xylene | 4.03 | 3.87 | 3.97 | 0.57 |
| C9+ | 6.05 | 6.22 | 5.96 | 6.25 |
| Conversion, wt % | | | | |
| Methanol | | 100 | | 100 |
| Benzene | | — | | — |
| Toluene | | 9.74 | | 11.08 |
| Ethyl benzene | | 84.58 | | 48.79 |
| Selectivity, wt % in Aromatics Products Formed | | | | |
| Benzene Formed | | 56.7 | | 95.5 |
| Mixed-Xylene Formed | | 41.3 | | — |
| C9+ Formed | | 2.0 | | 4.5 |
| p-X (formed) in formed mixed-xylene | | 92.3 | | — |
| Aromatic ring balance, % | | 98.0 | | 98.3 |

*LHSV based on aromatics + methanol feed

TABLE 5

| EXAMPLE | 7 | 8 |
|---|---|---|
| Catalyst | E | F |
| Catalyst load, ml | 5.40 | 5.40 |
| Catalyst load, g | 3.94 | 3.70 |
| Feed Rate | | |
| Aromatics, g/min | 0.3434 | 0.3240 |
| Methanol, g/min | 0.0094 | 0.0088 |
| H2 (Cofeed gas), cc/min | 840 | 790 |
| H2O as steam, g/min | 0.0619 | 0.062 |
| LHSV* | 4.48 | 4.23 |
| Reactor Inlet Pressure, psig | 23 | 24 |
| Average Catalyst Bed Temp/° C. | 511 | 508 |

TABLE 5-continued

| | Hours on stream | | | |
|---|---|---|---|---|
| | 31 | | 49 | |
| Stream Name | Feed | Product | Feed | Product |
| Stream Analysis, wt % | | | | |
| H2 | 13.87 | 14.88 | 13.34 | 13.86 |
| C1-C5 Nonaromatics | 0 | 2.81 | 0 | 1.95 |
| Water | 12.86 | 14.74 | 13.61 | 15.54 |
| Methanol | 1.95 | 0 | 1.94 | 0 |
| Benzene | 2.50 | 6.64 | 2.49 | 6.22 |
| Heptane | 0 | 0 | 0 | 0 |
| Toluene | 41.42 | 37.40 | 41.29 | 38.29 |
| Ethyl benzene | 8.24 | 5.16 | 8.21 | 5.10 |
| p-Xylene | 2.39 | 7.68 | 2.38 | 7.88 |
| m-xylene | 6.64 | 4.23 | 6.62 | 4.36 |
| o-Xylene | 4.06 | 0.35 | 4.04 | 0.47 |
| C9+ | 6.09 | 6.11 | 6.07 | 6.33 |
| Conversion, wt % | | | | |
| Methanol | | 100 | | 100 |
| Benzene | | — | | — |
| Toluene | | 7.91 | | 6.06 |
| Ethyl benzene | | 36.09 | | 37.10 |
| Selectivity, wt % in Aromatics Products Formed | | | | |
| Benzene Formed | | 96.7 | | 91.65 |
| Mixed-Xylene Formed | | — | | — |
| C9+ Formed | | 3.3 | | 8.35 |
| p-X (formed) in formed mixed-xylene | | — | | — |
| Aromatic ring balance, % | | 98.2 | | 99.2 |

*LHSV based on aromatics + methanol feed

As shown earlier, Catalysts A, B, and C were made differently than Catalysts D, E and F. The preparation of Catalysts D-F involved treatment of P-modified zeolite with liquid water prior to forming the modified zeolite powder into the shaped catalyst. Although not wishing to be bound by theory, the inventors suspect that this resulted in a significant increase in surface area and total pore volume, and also altered the Al environment in the zeolite structure. Catalysts A-C when used with benzene depleted pygas aromatics mixed with methanol, the catalysts showed formation of mixed xylene with greater than 85% p-xylene in the mixed xylene. In contrast, the Catalyst D, E and F showed formation of benzene with little or no xylene formation. No net change in the aromatic ring content was observed for either group of catalysts. For the second group of catalysts the use of methanol in the feed was optional.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of converting hydrocarbons comprising:
   a. contacting a hydrocarbon stream containing alkylated aromatic hydrocarbons with a catalyst of a first phosphorus-containing pentasil zeolite in a reactor, said phosphorus-containing pentasil zeolite having:
      i. a phosphorus content of 7.5% or less by weight of zeolite;
      ii. a pore volume of at least 0.2 ml/g; and
      iii. a $^{27}$Al MAS NMR spectrum characterized by a peak at or near 50 ppm that is greater than any other peak in said spectrum; and
   b. converting at least a portion of the alkylated aromatic hydrocarbons to benzene and recovering a benzene-enriched output stream from the reactor.

2. The method of claim 1, wherein the hydrocarbon stream contains benzene in an amount of less than 15% by weight of the feed and at least one of toluene, $C_8$ aromatics, and $C_{9+}$ aromatics in an amount totaling 50% or more by weight of the hydrocarbon stream.

3. The method of claim 2, further comprising separating benzene from the benzene-enriched output stream to form a benzene product stream and a second output stream.

4. The method of claim 3, further comprising contacting said second output stream with a xylene-selective catalyst in a second reactor to form a xylene-enriched output stream.

5. The method of claim 4, further comprising separating xylene from the said xylene-enriched output stream to form a xylene product stream.

6. The method of claim 4, wherein said xylene selective catalyst is a second phosphorus-containing zeolite that is bound with an inorganic binder, the second phosphorus-containing zeolite of the xylene selective catalyst having at least two $^{31}$P MAS NMR peaks with maxima at from 0 ppm to −55 ppm, with at least one $^{31}$P MAS NMR peak having a maximum at from −40 ppm to −50 ppm.

7. The method of claim 1, wherein said first phosphorus-containing pentasil zeolite has a phosphorus content of 0.1 to 4.5% by weight of zeolite.

8. The method of claim 1, wherein said first phosphorus-containing pentasil zeolite has a phosphorus content of 0.1 to 2% by weight of zeolite.

9. The method of claim 1, wherein said first phosphorus-containing pentasil zeolite has a silica to alumina molar ratio of at least 25.

10. The method of claim 1, wherein said first phosphorus-containing pentasil zeolite has a silica to alumina molar ratio of at least 200.

11. The method of claim 1, wherein:
    the hydrocarbon stream is a benzene-depleted pyrolysis gasoline stream.

12. The method of claim 1, wherein:
    the hydrocarbon stream contains toluene in an amount of from 40% to 65% by weight of the hydrocarbon stream.

13. The method of claim 1, wherein:
    the hydrocarbon stream contains $C_8$ aromatics in an amount of from 20% to 30% by weight of the hydrocarbon stream.

14. The method of claim 1, wherein:
    the hydrocarbon stream contains $C_{9+}$ aromatics in an amount of from 5% to 20% by weight of the hydrocarbon stream.

15. The method of claim 1, wherein:
    the hydrocarbon stream is a pyrolysis gasoline stream.

16. The method of claim 15, wherein:
    the pyrolysis gasoline stream contains benzene in an amount of less than 15% by weight of the feed and at least one of toluene, $C_8$ aromatics, and $C_{9+}$ aromatics in an amount totaling 50% or more by weight of the hydrocarbon stream.

17. The method of claim 16, further comprising separating benzene from the benzene-enriched output stream to form a benzene product stream and a second output stream.

18. The method of claim 17, further comprising contacting said second output stream with a xylene-selective catalyst in a second reactor to form a xylene-enriched output stream.

19. The method of claim 18, further comprising separating xylene from the said xylene-enriched output stream to form a xylene product stream.

20. The method of claim 19, wherein said xylene selective catalyst is a second phosphorus-containing zeolite bound with an inorganic binder, the second phosphorus-containing zeolite of the xylene selective catalyst having at least two $^{31}$P MAS NMR peaks with maxima at from 0 ppm to −55 ppm, with at least one $^{31}$P MAS NMR peak having a maximum at from −40 ppm to −50 ppm.

\* \* \* \* \*